United States Patent [19]

Green

[11] Patent Number: 4,806,354

[45] Date of Patent: Feb. 21, 1989

[54] HEALTH FOOD COMPOSITION

[76] Inventor: James P. Green, 176 Beckford Dr., Henderson, N.C. 27536

[21] Appl. No.: 933,562

[22] Filed: Nov. 21, 1986

Related U.S. Application Data

[63] Continuation-in-part of Ser. No. 597,591, Apr. 6, 1984, abandoned.

[51] Int. Cl.$^4$ ............... A61K 33/86; A61K 31/70; A61K 35/525; A61K 31/51
[52] U.S. Cl. ............................. 424/154; 514/52; 514/251; 514/276; 514/277; 514/458; 514/560; 514/579
[58] Field of Search ............... 424/154, 195.1; 514/52, 514/251, 276, 277, 458, 579, 560

[56] References Cited

U.S. PATENT DOCUMENTS

| | | | |
|---|---|---|---|
| 4,118,512 | 10/1978 | Eichelburg | 514/773 |
| 4,394,377 | 7/1983 | Spires | 514/459 |
| 4,497,800 | 2/1985 | Larson et al. | 514/2 |
| 4,582,705 | 4/1986 | Prines | 424/141 |

Primary Examiner—John W. Rollins
Attorney, Agent, or Firm—R. Martin Oliveras

[57] ABSTRACT

An improved health food composition comprises; B complex vitamins; a prostaglandin E-1 precursor; a primary emulsifying agent; a flavoring agent; and a preservative. The B complex vitamins include: vitamin B1 (thiamine hydrochloride); vitamin B2 (riboflavin); pantothenic acid; vitamin B6 (pyridoxine hydrochloride); and vitamin B12 (cyanocobalamin). The prostaglandin E-1 precursor may be safflower oil. The primary emulsifying agent is selected from the group consisting of: Poly Sorbate-80; acacia; sodium alginate; carbomer (carboxypolymethylene); carboxymethylcellulose; and others. The flavoring agent is selected from the group consisting of: orange; lemon; and peppermint. The preservative is selected from the group consisting of: sodium benzoate; alcohol; ethyl paraben; ethyl vanillin; glycerin; and others. The improved health fod composition may further comprise a secondary emulsifying agent being selected from the group consisting of: hydroxyethyl cellulose; hydroxypropyl cellulose; and tragacanth. The improved health food composition may further include an antioxidant being selected from the group consisting of: ascorbyl palmitate; butylated hydroxyanisole; butylated hydroxytoluene; sodium bisulfite; sodium metabisulfite; and others. Finally, the improved health food composition may further comprise an antacid such as calcium carbonate; and an analgesic such as acetaminophen.

8 Claims, No Drawings

HEALTH FOOD COMPOSITION

OTHER RELATED APPLICATIONS

This is a continuing-in-part application of application Ser. No. 06/597,591, filed 4/6/84, now abandoned, and entitled "Health Food Composition" by the same inventor herein.

FIELD OF THE PRESENT INVENTION

This invention relates to health food compositions and in particular to such compositions which include a precursor of prostaglandin E-1.

DISCUSSION OF THE PRIOR ART

The prior art reveals various so-called food or nutritional supplements as follows:

a. Fox et al U.S. Pat. No. 2,433,688 entitled "Multivitamin Preparation And Method of Producing Same" discloses the preparation comprising preformed nicotinamide ascorbate and other vitamins made from ascorbic acid and a nicotinamide base;

b. Fricke U.S. Pat. No. 2,694,668 entitled "Liquid Multiple Vitamin Preparation And Process Of Preparing The Same" discloses a preparation consisting of a stable oil-in-water emulsion having an aqueous continuous phase and an oil dispersed phase, the continuous phase comprising a corn syrup solution having water soluble vitamins dissolved therein including thiamine and ascorbic acid, and the dispersed phase comprising an oil solution having oil soluble vitamins dissolved therein including vitamin A;

c. Bash et al U.S. Pat. No. 2,764,484 entitled "Food Supplements And Process Of Preparing The Same" discloses the method of preparing homogeneous integrated particles of table salt including a minor proportion of vitamins;

d. Aterno et al U.S. Pat. No. 2,811,483 entitled "Pharmaceutical Composition And Process For Preparing The Same" discloses a plurality of discrete beadlets each having a hard spherical core of edible sugar containing material;

e. Larde U.S. Pat. No. 2,980,588 entitled "Multivitamin Preparation And Method Of Making Same" discloses a preparation containing fat soluble and water soluble vitamins further comprising a mixture of gel composed of vegetable oil gelled by the addition of colloidal silica;

f. Magid U.S. Pat. No. 3,332,848 entitled "Microcrystalline Cellulose With Starch In Niacinamide Ascorbic Acid Tablet Granulations" discloses a granulation consisting of niacin amide-ascorbic acid, vegetable starch, and microcrystalline cellulose; and g. Magid U.S. Pat. No. 3,777,029 entitled "Chewable Multivitamin Tablets Containing Aluminum Nicotinate" discloses a multivitamin premix composition containing a niacine active ingredient being aluminum nicotinate.

Based on the above prior art food or nutritional supplements, it does not appear that the present improved health food composition is disclosed by same.

Objects of the present invention are therefore:

a. to provide an improved health food composition which contains B complex vitamins and a prostaglandin E-1 precursor as a source of prostaglandin E-1 to supplement the diet; and b. to provide a dietery replacement which is necessary in the dietery and nutritional depletion states seen after excessive indulgence in alcohol.

SUMMARY AND FEATURES OF THE PRESENT INVENTION

A summary and features of the present invention are that:

a. the improved health food composition comprises: B complex vitamins; a prostaglandin E-1 precursor; a primary emulsifying agent; a flavoring agent; and a preservative agent;

b. the B complex vitamins include: vitamin B1 (thiamine hydrochloride); vitamin B2 (riboflavin); pantothenic acid; vitamin B6 (pyridoxine HCl); and vitamin B12 (cyanocobalamin);

c. the prostaglandin E-1 precursor may be safflower oil;

d. the primary emulsifying agent is selected from the group consisting of: Poly Sorbate-80; acacia; sodium alginate; carbomer (carboxypolymethylene); carboxymethylcellulose; sodium carboxymethylcellulose; carageenan; cholesterol; chondrus; gelatin type A or gelatin type B; glycerol monostearate; glyceryl monostearate; magnesium hydroxide; malt or malt extract; octylphenoxy polyethoxyethanol; oleyl alcohol; polyethylene glycol 400 monostearate; polyoxyethylene alkyl phenol; polyoxyethylene castor oil; polyoxyethylene lauryl ester; polyoxyethylene monostearate; polyoxyethylene sorbitan monolaurate; polyoxyethylene sorbitan monooleate; polyoxyethylene sorbitan monopalmitate; propylene glycol monolaurate; propylene glycol monostearate; sodium oleate; sorbitan monolaurate; sorbitan monooleate; sorbitan monopalmitate; sorbitan monostearate; sorbitan sesquioleate; sorbitan trioleate; sorbitan tristearate; and xanthum gum;

e. the flavoring agent is selected from the group consisting of: orange; lemon; and peppermint;

f. the preservative is selected from the group consisting of: sodium benzoate; alcohol; ethyl paraben; ethyl vanillin; glycerin; methyl paraben; phenol; phenylethyl alcohol; potassium sorbate; propylene glycol; propyl gallate; propyl paraben; sassafras oil; and sorbitol;

g. the improved health food composition may further comprise a secondary emulsifying agent being selected from the group consisting of: hydroxyethyl cellulose; hydroxypropyl cellulose; and tragacanth;

h. the improved health food composition may further comprise an antioxidant being selected from the group consisting of: ascorbyl palmitate; butylated hydroxyanisole; butylated hydroxytoluene; sodium bisulfite; sodium metabisulfite; ascorbic acid; sodium ascorbate; citric acid; sodium citrate; and alpha tocopherol;

i. the improved health food composition may further comprise an antacid such as calcium carbonate; and an analgesic such as acetaminophen;

j. the improved health food composition may comprise such B complex vitamins in the following amounts; vitamin B1: 100 to 200 mg.; vitamin B2: 100 to 200 mg.; panothenic acid: 100 to 200 mg.; vitamin B6: 100 to 200 mg.; and vitamin B12: 800 to 1,000 micrograms;

k. the improved health food composition may comprise such B complex vitamins in the following specific amounts: vitamin B1: 100 mg.; vitamin B2: 100 mg.; pantothenic acid: 100 mg.; vitamin B6: 100 mg.; and vitamin B12: 800 micrograms;

l. the improved health food composition may comprise such prostaglandin E-1 precursor as safflower oil in the amount of about 15 to 30 cc;

m. the improved health food composition may comprise such B complex vitamins in the following ratios: vitamin B1 in the ratio of 1/7 to 2/5 of the total weight of such B complex vitamins; vitamin B2 in the ratio of 1/7 to 2/5 of the total weight of such B complex vitamins; pantothenic acid in the ratio of 1/7 to 2/5 of the total weight of such B complex vitamins; and vitamin B6 in ratio of 1/7 to 2/5 of the total weight of such B complex vitamins;

n. such prostaglandin E-1 precursor may be selected from the group consisting of: safflower oil; peanut oil; sunflower seed oil; and vegetable oil; such prostaglandin E-1 precursor being 15 cc for each 1200 mg. weight of such B complex vitamins; and such prostaglandin E-1 precursor being up to 30 cc for each 1800 mg. weight of such B complex vitamins; and o. such improved health food composition may further comprise: 840 mg. of calcium carbonate antacid for each 15 cc of such prostaglandin E-1 precursor and 300 mg. of acetaminophen analgesic for each 15 cc of such prostaglandin E-1 precursor.

Advantages of the present invention are therefore that:

a. it is in a palatable and a digestable form;

b. the prostaglandin E-1 precursor component of the present improved health food composition helps to resolve neuromuscular tremors, gastrointestinal upsets, headaches, and generalized aches such as seen in the so-called hangover state after alcohol ingestion;

c. the B complex vitamin component of the present improved health food composition helps to replace those vitamins which are depleted after alcohol ingestion;

d. the acetominophen component of the present improved health food composition acts as an analgesic and helps to relieve some of the generalized aches and pains which occur after alcohol ingestion;

e. the calcium carbonate component of the present improved health food composition acts as an antacid to help reduce the gastrointestinal upset and nausea after alcohol ingestion;

f. the components of the present improved health food composition are readily available in the market place but when formulated according to the present invention help resolve such neuromuscular tremors, incoordination, fatigue, headaches, generalized muscle aches, upset stomach, all seen during the so-called hangover state after alcohol ingestion;

g. the safflower oil component of the present improved health food composition acts as the source of linoleic acid being the precursor of prostaglandin E-1 which is depleted after alcohol ingestion;

h. the present improved health food composition helps to alleviate symptoms of alcohol intoxication including heartburn, tremor, equilibrium disturbances, fatigue, dullness, depression, and irritability; and i. the present improved health food composition is a dietary aid to speed the recovery from so-called hangover state after alcohol ingestion to a normal baseline.

DETAILED DESCRIPTION OF THE PRESENT INVENTION

The above and other objects, features, and advantages of the present invention will be better appreciated from a reading of the following detailed description.

The B complex vitamins are necessary components of normal body functions. Such vitamins are usually obtained from dietary sources including liver and yeast. Deficiencies of B complex vitamins are seen in alcoholism causing disturbances in the proper functioning of the central nervous system. For example, thiamine deficiency may lead to nervousness, fatigability, personality disturbances, irritability, poor concentration, and impaired memory. Essential fatty acids are also necessary components of normal body functions. The three primary essential fatty acids are: linoleic, linolenic, and arachidonic acids. Both linolonic and arachidonic acids are made in the body from linoleic acid thereby making linoleic acid the primary essential fatty acid. The best known sources of linoleic and linolenic acids are vegetable oils such as soyabean and safflower oils. Arachidonic acid is known to be an essential fatty acid precursor of prostaglandins. It is believed that prostaglandins have cytoprotective effects on the cells of the gastrointestinal tract which have been exposed to damaging substances such as alcohol.

For many reasons it is not practical to ingest naturally occurring prostaglandins such as PGE 1 or PGE 2. Consequently, considerable attention has focused on the use of prostaglandin precursors including linolenic acid, y-linolenic acid (GLA), and dihomo-y-linolenic acid (DGLA).

The broad outline of the prostaglandin pathway is well known and clearly shows that a major function of essential fatty acids (EFA) are to act as precursors for prostaglandins. Prostaglandins in the 1-series are formed from dihomo-y-linolenic acid (DGLA) and 2-series prostaglandins are formed from arachidonic acid (AA). DGLA and AA are present in food only in small quantities, and the major EFA in food is linoleic acid. Linoleic acid is first converted to y-linolenic acid, then to GLA, and then to DGLA and AA. The conversion of linolenic acid to GLA may be blocked by a high fat and a high carbohydrate diet content, by aging, and by diabetes. Stores of AA in the body in the form of lipid esters are very large. In contrast, only small amounts of DGLA esters are present in body stores.

DGLA is the key substance. GLA is almost completely and very rapidly converted in the body to DGLA. So, for practical purposes, the oral administration of DGLA and GLA is substantially identical. DGLA can be converted to a form which is stored, then changed to arachidonic acid, and then to prostaglandins of the 2-series, or converted to prostaglandins of the 1-series. Prostaglandin E-1 reduces stomach acid secretion, reduces motility of the gastrointestinal tract, and protects the gastrointestinal tract from certain exogenous substances. See, for example, Sinar, *Prostaglandin Influences On The Gastrointestinal Tract, Current Concepts In Gastroenterology*, July/August 1983, pages 33–36.

The improved health food composition according to the present invention comprises: B complex vitamins; a prostaglandin E-1 precursor; a primary emulsifying agent; a flavoring agent; and a preservative. The B complex vitamins include: vitamin B1 (thiamine hydrochloride); vitamin B2 (riboflavin); pantothenic acid; vitamin B6 (pyridoxine HCl); and vitamin B12 (cyanocobalamin). The prostaglandin E-1 precursor may be safflower oil. The primary emulsifying agent is selected from the group consisting of: Poly Sorbate-80; acacia; sodium alginate; carbomer (carboxypolymethylene), carboxymethylcellulose; sodium carboxymethylcellulose; carageenan; cholesterol; chondrus; gelatin type A or gelatin type B; glycerol monostearate; glyceryl monostearate; magnesium hydroxide; malt or malt extract; octylphenoxy polyethoxyethanol; oleyl alcohol; polyethylene glycol 400 monostearate; polyoxyethylene alkyl phenol; polyoxyethylene castor oil; polyoxyethylene lauryl ester; polyoxyethylene monostearate; polyoxyethylene sorbitan monolaurate; polyoxyehtylene sorbitan monooleate; polyoxyethylene sorbitan monopalmitate; propylene glycol monolaurate; propylene glycol monostearate; sodium oleate; sorbitan monolaurate; sorbitan monooleate; sorbitan monopalmitate; sorbitan monostearate; sorbitan sesquioleate; sorbitan trioleate; sorbitan tristearate; and xanthum gum. The flavoring agent is selected from the group consisting of: orange; lemon; and peppermint. The preservative is selected from the group consisting of: sodium benzoate; alcohol; ethyl paraben; ethyl vanillin; glycerin; methyl paraben; phenol; phenylethyl alcohol; potassium sorbate; propylene glycol; propyl gallate; propyl paraben; sassafras oil; and sorbitol. The improved health food composition may further comprise a secondary emulsifying agent acting as a stabilizer being selected from the group consisting of: hydroxyethyl cellulose; hydroxypropyl cellulose; and tragacanth. The improved health food composition may further comprise an antioxidant being selected from the group consisting of: ascorbyl palmitate; butylated hydroxyanisole; butylated hydroxytoluene; sodium bisulfite; sodium metabisulfite; ascorbic acid; sodium ascorbate; citric acid; sodium citrate; and alpha tocopherol. The improved health food composition may further comprise an antacid such as calcium carbonate; and an analgesic such as acetaminophen.

The improved health food composition may comprise such B complex vitamins in the following amounts: vitamin B1: 100 to 200 mg.; vitamin B2: 100 to 200 mg.; panothenic acid: 100 to 200 mg.; vitamin B6: 100 to 200 mg.; and vitamin B12: 800 to 1,000 micrograms. The improved health food composition may comprise such B complex vitamins in the following specific amounts: vitamin B1: 100 mg.; vitamin B2: 100 mg.; pantothenic acid: 100 mg.; vitamin B6: 100 mg.; and vitamin B12: 800 micrograms. The improved health food composition may comprise such safflower oil in the amount of about 15 to 30 cc. The improved health food composition may comprise such B complex vitamins in the following ratios: vitamin B1 in the ratio of 1/7 to 2/5 of the total weight of such B complex vitamins; vitamin B2 in the ratio of 1/7 to 2/5 of the total weight of such B complex vitamins; pantothenic acid in the ratio of 1/7 to 2/5 of the total weight of such B complex vitamins; and vitamin B6 in ratio of 1/7 to 2/5 of the total weight of such B complex vitamins. Such prostaglandin E-1 precursor may be selected from the group consisting of: safflower oil; peanut oil; sunflower seed oil; and vegetable oil being 15 cc for each 1200 mg. weight of such B complex vitamins; and being up to 30 cc for each 1800 mg. weight of such B complex vitamins. Such improved health food composition may further comprise: 840 mg. of calcium carbonate antacid for each 15 cc of such prostaglandin E-1 precursor and 300 mg. of acetaminophen for each 15 cc of such prostaglandin E-1 precursor. The preservative selected may be sodium benzoate being 0.15% by weight of such total composition.

The prostaglandin E-1 precursor according to the present invention is supplied by the addition of safflower oil. Safflower oil is composed of about 85% linoleic acid, a known prostaglandin precursor. The acceptable dosage range of prostaglandin E-1 is contained in about 15 to 30 cc of safflower oil. However, the optimum dose of prostaglandin E-1 is contained in about 15 cc of safflower oil.

While safflower oil is the preferred source for the precursor of prostaglandin E-1, other known sources of prostaglandin E-1 may be substituted for safflower oil such as peanut oil and other vegetable oils.

The improved health food composition according to the present invention is preferably in liquid form, although it is suitable for manufacture in capsule form as well. A daily intake of about ½ ounce of liquid containing the B complex vitamins and the prostaglandin E-1 precursor in the aforementioned amounts is an effective dose. It is further recommended that such effective dose be ingested once or twice weekly.

Clinical studies relating to the subject improved health food composition have shown the following:

a. over 35% of individuals who became intoxicated demonstrated impaired driving in the hangover state even after their blood alcohol levels had returned to normal levels; and b. the majority of the subjects when tested during the hangover period after blood alcohol levels had returned to normal levels demonstrated unimpaired driving when the subject improved health food composition was ingested on the night of alcohol ingestion and on the morning following alcohol ingestion.

While the arrangement according to the present invention has been described in terms of a specific illustrative embodiment, it will be apparent to those skilled in the art that many modifications are possible within the spirit and scope of the disclosed principle.

What is claimed is:

1. An improved health food composition for alleviating the side effects experienced after alcohol ingestion, said composition comprising:
   a. B complex vitamins, said B complex vitamins further comprising: vitamin B1 in the amount of about 100 to 200 mg; vitamin B2 in the amount of about 100 to 200 mg; pantothenic acid in the amount of about 100 to 200 mg; vitamin B6 in the amount of about 100 to 200 mg; and vitamin B12 in the amount of about 800 to 1000 micrograms;
   b. a prostaglandin E-1 precursor being selected from the group consisting of: safflower oil, peanut oil, sunflower seed oil, and mixtures thereof; said precursor being in the amount of about 15 cc for each 1200 mg of said B complex vitamins; and said precursor being in the amount of up to about 30 cc for each 1800 mg of said B complex vitamins;
   c. an analgesic comprising acetaminophen, said analgesic being in the amount of about 300 mg for each 15 cc of said prostaglandin E-1 precursor; and
   d. an antacid comprising calcium carbonate, said antacid being in the amount of about 840 mg for each 15 cc of said prostaglandin E-1 precursor.

2. The improved health food composition of claim 1 further comprising a preservative sodium benzoate, said preservative being in the amount of about 0.15% by weight of said total improved health food composition.

3. The improved health food composition of claim 2 further comprising a primary emulsifying agent and a flavoring agent.

4. The improved health food composition of claim 3 further comprising a secondary emulsifying agent and an antioxidant.

5. An improved health food composition for alleviating the side effects experienced after alcohol ingestion, said compsition comprising:
   a. B complex vitamins, said B complex vitamins further comprising: vitamin B1 being in the amount of about 1/7 to 2/5 by weight of said B complex vitamins; vitamin B2 being in the amount of about 1/7 to 2/5 by weight of said B complex vitamins; pantothenic acid being in the amount of about 1/7 to 2/5 by weight of said B complex vitamins; and vitamin B6 being in the amount of about 1/7 to 2/5 by weight of said B complex vitamins;
   b. a prostaglandin E-1 precursor comprising: safflower oil, peanut oil, sunflower seed oil, and mixtures thereof; said precursor being in the amount of about 15 cc for each 1200 mg of said B complex vitamins; and said precursor being in the amount of up to about 30 cc for each 1800 mg of said B complex vitamins;
   c. an analgesic comprising acetaminophen, said analgesic being in the amount of about 300 mg for each 15 cc of said prostaglandin E-1 precursor; and
   d. an antacid being selected from the group consisting of calcium carbonate, said antacid being in the amount of about 840 mg for each 15 cc of said prostaglandin E-1 precursor.

6. The improved health food composition of claim 5 further comprising a preservative sodium benzoate, said preservative being in the amount of about 0.15% by weight of said total improved health food composition.

7. The improved health food composition of claim 6 further comprising a primary emulsifying agent and a flavoring agent.

8. The improved health food composition of claim 7 further comprising a secondary emulsifying agent and an antioxidant.

* * * * *